United States Patent [19]

Jayaraman

[11] Patent Number: 5,298,276
[45] Date of Patent: Mar. 29, 1994

[54] PROCESS FOR PRODUCING ARTIFICIAL BLOOD VESSELS OF CONTROLLED PERMEABILITY AND PRODUCT PRODUCED THEREBY

[76] Inventor: Swaminathan Jayaraman, 6703 Pemberton Oaks Ct., Seffner, Fla. 33584

[21] Appl. No.: 859,909

[22] Filed: Mar. 30, 1992

Related U.S. Application Data

[63] Continuation-in-part of Ser. No. 571,933, Aug. 24, 1990, abandoned.

[51] Int. Cl.$^5$ .......................... A61F 2/06; A61K 9/70
[52] U.S. Cl. .......................... 427/2; 623/1; 427/365
[58] Field of Search .............. 427/2, 365, 322, 412, 427/538; 623/1

[56] References Cited

U.S. PATENT DOCUMENTS

| | | | |
|---|---|---|---|
| 2,838,799 | 6/1958 | Meister | 427/365 |
| 3,729,007 | 4/1973 | Mirkovitch | 427/2 |
| 4,605,406 | 8/1986 | Cahalan et al. | 623/1 |
| 4,670,286 | 6/1987 | Nyilas et al. | 427/2 |
| 4,687,482 | 8/1987 | Hanson | 623/1 |
| 4,695,280 | 9/1987 | Watanabe et al. | 623/1 |
| 4,816,028 | 3/1989 | Kapadia et al. | 623/1 |
| 4,851,009 | 7/1989 | Pinchuk | 427/2 |
| 4,871,361 | 10/1989 | Kira | 427/2 |
| 4,902,290 | 2/1990 | Fleckenstein et al. | 427/2 |
| 4,911,713 | 3/1990 | Sauvage et al. | 623/1 |
| 5,026,607 | 6/1991 | Kiezulas | 427/2 |
| 5,108,424 | 4/1992 | Hoffman, Jr. et al. | 623/1 |
| 5,192,310 | 3/1993 | Herweck et al. | 623/1 |

Primary Examiner—Shrive Beck
Assistant Examiner—Diana Dudash
Attorney, Agent, or Firm—Herbert W. Larson

[57] ABSTRACT

The process described herein involves the production of artificial blood vessels starting with a tue knit or woven from polmeric fibers such as polyester, for example, polyethyleneterephthalate, which has been surface cleaned and then coated on the exterior surface of the tube with one or more layers as defined more fully hereinafter of polysiloxane, polyurethane or a block copolymer of polyurethane and polysiloxane to give the desired amount of permeability. A preferred block copolymer is made an hydroxyalkyl-terminated polysiloxane and a polyurethane. The coating material is preferably applied by pressurized application to give an impermeable or almost impermeable layer on the outside of the tube and then the coated tube is solvent treated to remove enough of the coating to give the desired amount of permeability, preferably a porosity that is measured to permit 1-25, preferably 1-5 milliliters or cubic centimeters of water to flow through 1 square centimeter of surface area of the tube with water under a pressure of 120 mm. of mercury. The solvent treatment not only reduces the permeability but also removes polymeric coating material from the inside of the tube thereby preferably leaving exposed polymeric fibers on the inside of the tube and coating material in the interstices and on the outside of the tube.

21 Claims, 5 Drawing Sheets

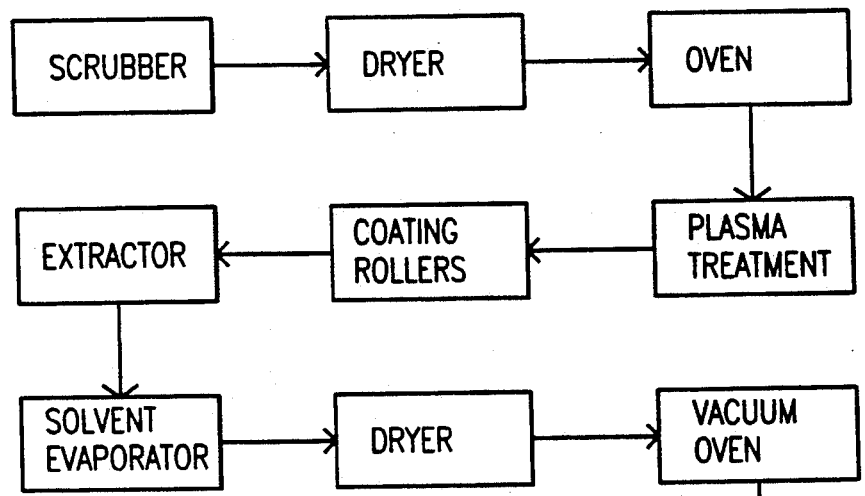
Fig. 1
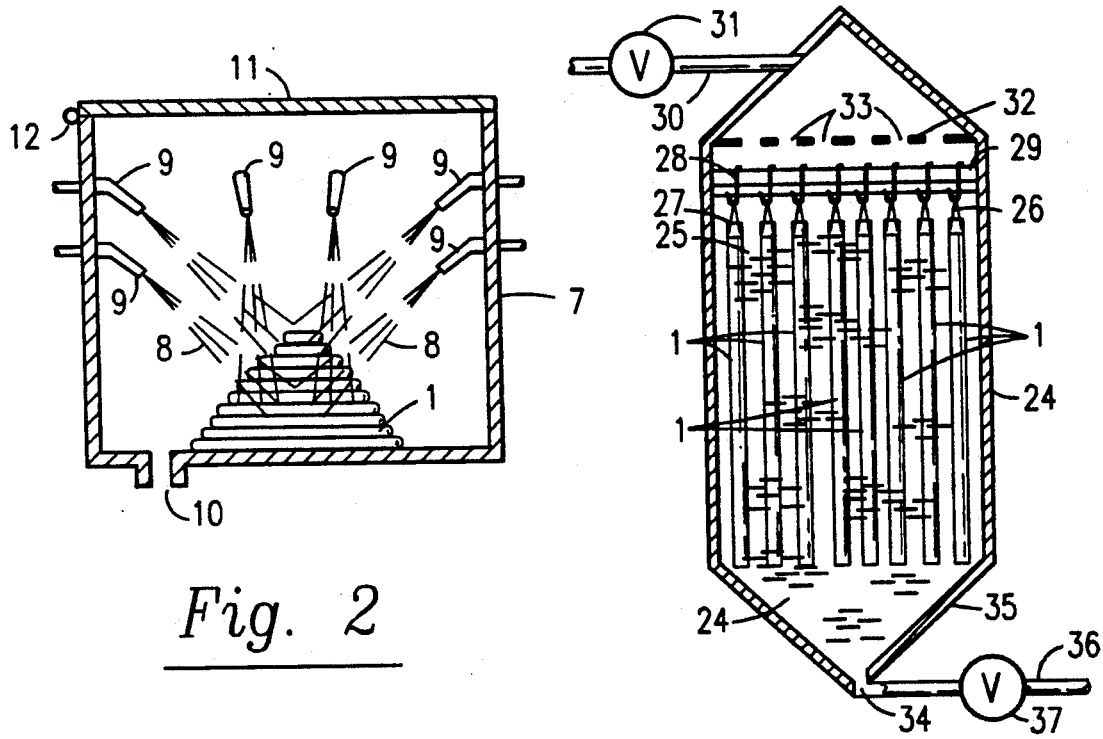
Fig. 2
Fig. 8

PROCESS FOR PRODUCING ARTIFICIAL BLOOD VESSELS OF CONTROLLED PERMEABILITY AND PRODUCT PRODUCED THEREBY

This application is a continuation-in-part of application Ser. No. 07/571,933 filed Aug. 24, 1990 and now abandoned.

STATE OF THE PRIOR ART

There is extensive prior art on the use of various polymeric materials in knit, woven or other forms as artificial grafts for blood vessels. Tubes of polyurethanes, polysiloxanes and block copolymers of a polyurethane and a polysiloxane have been attempted for such purposes. The attempts at such manufacture have been primitive and unsuccessful. There have also been disclosed various problems arising from the use of such tubes as grafts, such as blood clotting, occlusion, and other side reactions. Currently used textile blood vessels generally have permeabilities or porosities too high to be effective. Therefore before using these, the surgeon has to preclot the same. In the preclotting procedure the artificial blood vessel is allowed to stand for about 45–60 minutes in blood taken from the patient. This preclotting procedure has the effect of reducing permeability to the desired range of about 1–25 permeability. Permeability is determined as the amount of water (milliliters or cubic centimeters) passed through one square centimeter of the surface in contact with water under a pressure of 120 millimeters of mercury. The artificial blood vessels of the present invention have a permeability in the range of 1–25, preferably 1–5, and do not need to be pre-clotted before being implanted in a patient's body.

BACKGROUND OF THE INVENTION

Field of the Invention

This invention relates to a process for fabricating artificial blood vessels that may be grafted as a substitute or to replace a portion of a human blood vessel. More specifically it relates to an artificial blood vessel that approaches the properties of a human blood vessel in its various properties such as pulsatility, elasticity, compatibility to blood, compliance, permeability, etc. (Pulsatility is the ability of a blood vessel to develop sufficient pressure to cause blood to flow therethrough—too much permeability will allow blood flow through the pores and thereby hinder build-up of sufficient pressure to allow blood flow through the blood vessel. Elasticity in radial and longitudinal directions impart good pulsatility and compliance. Compatibility to blood relates to surface properties of the blood vessel—thus a more inactive surface means the blood vessel is more blood compatible whereas a more reactive surface means the surface interacts with the blood.) Still more specifically it relates to an artificial blood vessel and method for producing the same with controlled permeability to allow the passage of nutrients, ions, and other body fluid in a manner similar to that permitted by human blood vessels. Once this passage of ions, etc., is permitted by the artificial blood vessels, this acts as a precursor to the entire healing process and in return the graft remains open or patent for extended periods.

The following patents exemplify the prior art.

U.S. Pat. No. 3,562,352 describes block copolymers of either polyether urethanes or polyester urethanes and polysiloxanes, preferably poly(dimethylsiloxane). Example 11 describes the preparation of a tube having both inner and outer surfaces of the block copolymer of a polyether urethane—poly(dimethylsiloxane) from a solution in which the solvent is a combination of 1000 parts by weight of tetrahydrofuran per 1200 parts by weight of dioxane. "A precleaned, highly polished stainless steel mandril was dipped into solution and allowed to partially dry. While in a semidry condition, the tube while still on the mandril was wrapped with one layer of a number 20 Dacron mesh fabric presoaked in purified anhydrous tetrahydrofuran. The Dacron wrapped tube was then dipped into the block-copolymer solution to deposit an additional layer over the Dacron fabric. The tube while still on the mandril was allowed to dry completely at room temperature and subsequently maintained at 80° C. for one to two hours. It was removed from the mandril. Final dimensions of the tube are 1.8 cm. inside diameter, 12.5 cm. length and 0.03 cm. wall thickness." It is described as suitable, with appropriate sterilization, for use as a saturable aortic graft.

Sawyer U.S. Pat. No. 4,167,045 shows the production of cardiac and vascular prostheses which comprises a Dacron crimped vascular graft coated with protein applied from a protein solution. These were further modified by the addition of ground solid succinic anhydride. The grafts were hydrostatically tested to withstand 30 mm of Hg pressure "without showing evidence of air leaks through the graft pores" (Col. 7, lines 43–45). These grafts were also tested with various deposited powders, such as Agar, aluminum, etc. There is no indication of a control of or desired range of permeability.

U.S. Pat. No. 4,623,347 teaches the prevention of clotting of blood in contact with antithrombogenic elastomers prepared by mixing solutions of polyurethane and polysiloxane having reactive terminal groups and reacting them to produce a molded product therefrom. Films of such products were cast on the surface of a test tube. Patentee indicates that similar castings or molding may be used to cover the exposed surfaces of medical devices and instruments which come into direct contact with blood.

Nyilas U.S. Pat. No. 4,670,286 describes a vascular prosthesis of a bioresorbable material (polyglycolic acid) intertwined with nonresorbable (Dacron). The bioresorbable materials "become degraded and ultimately vanish, gradually increasing the biological porosity of the graft over its initial porosity." (Col. 4, lines 27–30). This involves a bioresorbable material which degrades and disappears so that after implantation shows an increase in porosity regardless of what it might have been originally. There is no disclosure of a controlled, desired low-initial permeability.

U.S. Pat. No. 4,675,361 also teaches polymer systems suitable for blood-contacting surfaces of a biomedical device. These systems comprise a base polymer, preferably a polyurethane, mixed with a block copolymer of polyurethane and polysiloxane. Example 4 describes a typical procedure using a solution of 99.0 weight percent of polyesterurethane and 0.1 weight percent silicone/polyurethane block copolymer in a solvent comprising 90% by volume of tetrahydrofurane and 10% dimethylformamide. This "solution is coated onto tapered stainless steel mandrels by multiple dipping. The solvent is allowed to evaporate and the film is removed from the mandrel. The resulting 'balloon' is mounted on a predrilled catheter and is useful as a cardiac arrest device when placed in the descending aorta and inflated and deflated with $CO_2$ in counterpulsation to the heart."

U.S. Pat. No. 4,685,280 describes an artificial vascular graft made of fibers in which the inner surface is made of fibers of less than 0.5 denier and the outer surface is made of fibers of more than 1.0 denier. Polymers specified are polyamides, polyurethanes, polyolefins and preferably polyesters. Other fibers may be mixed with these which are of a type such as polystyrene which may be removed or stripped, for example, by a solvent. This patent states in col. 3, lines 37–52:

"It is convenient to refer to the rate of water permeation as a standard measure. The phrase rate of water permeation, is defined here as the amount (ml/minute) of water permeating through 1 $cm^2$ of the surface of the grafts (or cloth) under 120 mm Hg of pressure.

To prevent blood leakage, this rate should be below 500 ml/min, and preferably below 100 ml/min. These values are only guides and it is unnecessary to adhere to them strictly. There may be many cases where artificial vascular grafts of this invention have rates of water permeation of 3000 and 5000 ml/min but are superior to conventional artificial vascular grafts in formation of intervascular endothelium and in utility for anastomosis. But performance of the artificial vascular grafts is particularly good when the rate of water permeation is low."

U.S. Pat. No. 4,731,073 shows an arterial graft prosthesis formed of a core zone of porous elastomer disposed about the longitudinal axis of the prosthesis, an inner zone of solid elastomer joined to the inner surface of the zone of porous elastomer, and an outer zone of solid elastomer, this outer zone of solid elastomer being joined to the outside of the zone of porous elastomer. There is little information as to the polymer compositions of the various layers although some zones are identified as polyether-polyurethane "having a lack of pores or orifices".

Pinchuk U.S. Pat. No. 4,851,009 shows the treatment of prostheses made of fibers of polyurethane, polypropylene and polymethacrylate with a silicone rubber to reduce or prevent surface fissuring or cracking and shows plasma pretreatment for grafting silicone polymers onto the substrate. The polyester of the present invention does not exhibit either surface fissuring or cracking.

Kira U.S. Pat. No. 4,871,361 describes an artificial blood vessel comprising two concentric layers made of an elastomer, the inner layer having a porosity of 80–95% and the other layer(s) having a lower porosity so that the overall porosity is 75–90%. This range of porosity is well above the permeability range of applicant's product, as described hereinafter, and will require blood preclotting to bring the product within the desired low permeability range, which preclotting is not necessary with applicant's product of the present invention. Moreover, Kiro's method of producing pores in his product is entirely different from applicant's. Kiro does not apply any coating but instead has a soluble substituent in his base material which, upon treatment with an appropriate solvent, is removed to leave openings or pores. Kiro does not aim for or teach a low porosity and if the soluble substituent is not completely removed by solvent treatment, this substituent will be leached out by the blood thereby eventually producing even higher porosity.

Fleckenstein et al disclose porous artificial blood vessels comprising polyethylene terephthalate fibers which have been impregnated with gelatin which is subsequently crosslinked with a diisocyanate. The gelatin, as well as collagen, albumin, etc., used as impregnants, all invoke immune responses in the body. Each of these materials is intended to degrade in the human body but in reality they do not degrade. Moreover coatings with biologic materials tend to flake off during or after implantation which is not the case with applicant's fabricated products.

None of these patents teach applicant's method of controlling or adjusting the permeability of an artificial vascular graft.

Permeability is an important property in facilitating the transmission of appropriate ions in body fluids passing into and out of the vascular system.

For general replacement of blood vessels it is desirable to have artificial blood vessels available with inside diameters ranging from 1 mm. to 34 mm. At present artificial blood vessels are available only with inside diameters of 8 mm. or greater. With tubes smaller than 8 mm. I.D. there are a number of problems which include high permeability leading to blood clotting, occlusion, etc. It is desirable therefore to be able to have artificial blood vessels in the full range including less than 8 mm. I.D. which have low, controlled optimum permeability which will avoid or minimize blood occlusion and clotting.

OBJECTIVES

It is an object of this invention to provide artificial blood vessels having properties appropriate for contact with blood.

It is also an object of this invention to provide artificial blood vessels having appropriate permeability to allow the transmission of nutrients, ions, etc., contained in body fluids through the walls of these artificial blood vessels.

It is also an object of this invention to provide artificial blood vessels of appropriate compliance and other desired properties to serve as a substitute for human blood vessels.

It is still further an object of this invention to provide artificial blood vessels made from fibers of a base polymeric material to provide the desired strength and other required characteristics.

It is still further an object of this invention to provide a base fabric to provide basic strength and suitable properties for contact with blood and a coating material on said fabric to control the permeability so as to aid in the transport of ions through the fabric material.

It is still further an object of this invention to provide a process for assembling the artificial blood vessels of the preceding objects and to control the permeability of these artificial blood vessels by the pressurized application of a coating material onto the exterior of these artificial blood vessels.

It is still further an object of this invention to provide a process for providing the desired low permeability of these artificial blood vessels and thereby avoiding any need for pre-clotting to bring the permeability to the desired range.

These and other objects that will become obvious from the description given hereinafter will be met by the present invention.

STATEMENT OF THE INVENTION

These objectives are met by the artificial blood vessels of this invention. These comprise a tube knit or woven from fibers of a base polymer, such as polyester, i.e., polyethyleneterephthalate, preferably of ultrafine fibers. Although such tubes made of fibers of convenient size, such as in the range of 40-130 denier, may be used, it is preferred to use tubes made of ultrafine fibers having size of 0.5-40 denier. The tubes are heat treated, as described more fully hereinafter, to produce crimps which are approximately perpendicular to the longitudinal axis of the tubes. The crimps may be either spiral or concentric. With concentric ridges each ridge may coincide with a plane which is perpendicular to the linear axis of the tube. With spiral ridges there is only approximate perpendicularity to the linear axis. With a large number of crimps per inch of the linear axis the approximate perpendicularity is close to true perpendicularity whereas with fewer ridges per inch the approximate perpendicularity is farther from true perpendicularity. Advantageously a tube has 8-14 ridges, preferably 8-12 ridges per inch in length of tubes and a depth of 0.02-0.03 inch, preferably 0.022-0.028 inch from top of ridge to bottom of valley between adjacent ridges. Reference hereinafter to "crimped tubes" includes tubes with either spiral or concentric configuration.

Such tubes are carefully surface cleaned, advantageously by plasma cleaning and one, two or three coatings applied, of either a polyurethane or a polysiloxane but preferably of a block copolymer of polyurethane and polyxiloxane.

In applying the respective coatings each tube is either fed through a pressurized chamber containing viscoelastic coating material or is fed substantially vertically downward between at least two pairs of rollers each arranged substantially horizontally. In each pair the two rollers are parallel and adapted to rotate in close proximity to the other roller of the pair. A first pair of rollers is arranged vertically above a second pair, and if there is a third pair of rollers, it is positioned vertically below the second pair. It may be preferred to use the combination of a pressurized chamber of viscoelastic coating material and rollers for pressing the coating material into the outer surface of a tube. It is contemplated that other methods of pressurized application would be suitable but those described herein are preferred.

While the pressure of the two rollers in a pair against the tube passing therebetween will cause some flattening of the ridges in the tube surface as the tube passes between the pair of rotating rollers, it is desirable to have the lower pair or pairs of rollers rotated at a greater speed than the pair of rollers above. In this way the pull on the tube because of this difference in rotation speed will flatten the ridges and present a flatten surface for application of the coating.

It is also desirable to have the axes of each respective pair of rollers pointed in a different direction from rollers in the pair directly underneath. For example, if the first pair of rollers has its axes pointed in an east-west direction, it would be advantageous to have the axes of the second pair of rollers pointed in another direction such as north-south. In such case it may be stated that the second pair of rollers is arranged in a 90° horizontal direction from the horizontal direction of the first pair of rollers. Moreover if three pairs of rollers are used, it may be desirable to have the second pair arranged at 60° from the horizontal direction of the first pair and the third pair arranged at 60° from the horizontal direction of the second pair. Thus the axes of the 1st pair may be set in an east-west direction, the second pair set in a northeast-southwest direction and the third pair in a southeast-northwest direction. Another alternative in a three pair arrangement of rollers would be to have the second pair of rollers in a southeast-northwest direction and the third pair in a northeast-southwest direction. These differences in axes directions assist in thoroughly coating the circumferential area around the tube.

The polymeric material is a soft, solid, viscoelastic material, advantageously having a viscosity in the range of 1,000-3,000 centipoises, preferably 1,500-2,500 centipoises, which can be pressed into the interstices of the woven or knitted tube described herein.

If a single layer of a polysiloxane is applied, the coating material must be applied in such an amount or thickness that by the time enough material has been impregnated into the pores to reduce the permeability to the desired amount the polysiloxane has penetrated completely through and is on the inner surface of the tube. In order to avoid this, when a first coating of polysiloxane is applied to the outer surface of the tube, this must be in a limited amount and this must be supplemented by second coating of another material, or a second and third coating of such other materials.

In order to obtain the desired range of permeability it has been found suitable to apply coatings as follow:
(a) a first layer of polysiloxane;
 a second layer of block copolymer (of polyurethane and polysiloxane); and
(b) a first layer of polysiloxane; and
 a second layer block copolymer;
(c) a first layer of polyurethane; and
 a second layer of block copolymer;
(d) a layer of only block copolymer;
(e) a first layer of polysiloxane; and
 a second layer of polyurethane;
(f) a first layer of polyurethane; and
 a second layer of polysiloxane;
(g) a layer of only polyurethane. If the coated tube does not have a sufficient reduction of permeability, additional coating of the last applied material may be added until the desired permeability is reached.

The coated product is treated with solvent to remove coating material in a controlled manner until the desired permeability has been obtained. If the coated tube is impermeable or has less than the desired permeability, then the coated tube is returned to the extractor to remove more of the coating. The desired permeability is advantageously in the range of 1-25 ccs, preferably in the range of 1-5 ccs of water per sq. cm of surface per minute when applied at room temperature under a pressure of 120 mm of Hg. Prior to the application of the coating material, the polyester fabric tubing has a permeability above 200, advantageously of 600-3,000, preferably 1,000-1,600.

Typical base polymers which may be used for fabricating the basic tubing are preferably polyester, i.e., polyethyleneterephthate and related materials but may also be polyurethanes, polysulfones, polycarbonates, polyethylene, polypropylene, polystyrene, poly(acrylonitrile-butadienestyrene), polybutadiene, polyisoprene, styrenebutadiene-styrene block copolymers, styreneisoprenestyrene block copolymers, poly-4-methylpentene, polyisobutylene, polymethyl-methacrylate, polyvinylacetate, polyacrylonitrile, polyvinyl chloride, cellulose and its esters and derivatives, and the like.

The polymeric material used as the coating material is preferably a block copolymer of polysiloxane and polyurethane but polysiloxanes and polyurethanes may also be used. In the scope of the block copolymers there may be included blocks of polysiloxane and monomeric urethane which can be derived by the reaction of a diisocyanate with a polysiloxane having terminal hydroxyalkyl, hydroxyaryl, hydroxycycloalkyl, aminoalkyl, aminoaryl or aminocycloalkyl groups, referred to generically as hydroxyhydrocarbyl and aminohydrocarbyl groups. The block copolymer may also be derived from a polysiloxane having said terminal hydroxyhydrocarbyl or amino hydrocarbyl groups with a polyurethane having terminal isocyanate groups. These various polymers may be used individually or in mixtures of various combinations of such materials.

The block copolymers may be represented by the formula (A-B)$_x$ in which A represents alternating segments of polysiloxane (soft, elastomeric segments) and B represents alternating segments of polyurethane, which are hard segments providing stability and mechanical enhancement. The soft segments (polysiloxane) and the hard segments (polyurethane) are phase separated and give their characteristic properties to the copolymer.

The polysiloxane segment is preferably an hydroxybutyl-terminated poly(chloropropylmethyl siloxane)

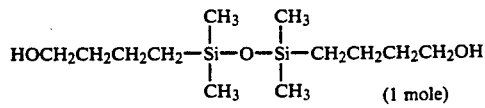

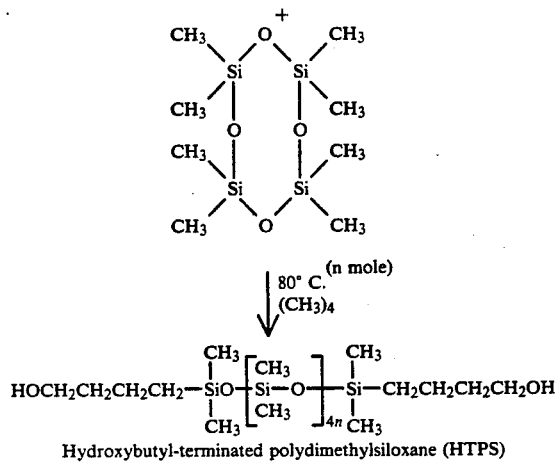

Hydroxybutyl-terminated polydimethylsiloxane (HTPS)

This hydroxybutyl-terminated polydimethylsiloxane is reacted with m moles of a diisocyanate such as 1,4-diphenylmethane diisocyanate preferably at about 70° C. and catalyzed by dimethylacetamide (DMAC) to give:

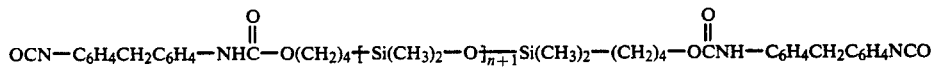

or an hydroxybutyl-terminated poly(dimethylsiloxane) which has respective the following repeating units:

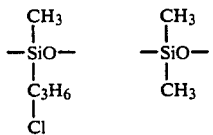

"X" is an integer having a value of 1–500, preferably 1–250.

The polyurethane segment is preferably derived from 4,4'-diphenylmethanediisocyanate and either 1,4-butanediol or N-methyldiethanolamine which have respectively the following formulas:

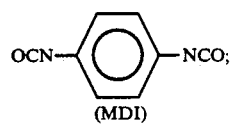

HO—CH$_2$CH$_2$CH$_2$CH$_2$OH;

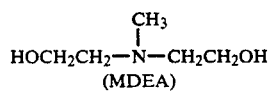

In a preferred modification a polysiloxane segment may be prepared by the reaction of 1,3-bis(4-hydroxybutyl)tetramethyldisiloxane with octamethylcyclotetrasiloxane as illustrated in the following reaction:

This product may be reacted with m' moles of a chain extender such as N-methyldiethanolamine (MDEA) or 1,4-butane-diol (BD) to give the general formulas:

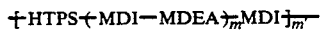 (I)

or $+$HTPS$+$MDI—MDEA$\rightarrow_{m'}$MDI$\rightarrow_{m}-$

As indicated above this block copolymer is used to coat the fiber mesh, knit or weave used as the core of the artificial blood vessel and this coating effects control of the permeability of the artificial blood vessel.

BRIEF DESCRIPTION OF THE DRAWINGS

The description of the invention is facilitated by reference to the drawings.

FIG. 1 is a flow sheet of the procedure steps of a preferred modification of the invention.

FIG. 2 is a cross-sectional elevational view of a scrubber used for cleaning a tube prior to a coating operation.

FIG. 8 is a cross-sectional elevational view of solvent extractor used to treat the coated tube.

DESCRIPTION OF THE PREFERRED EMBODIMENTS

Figure 3:
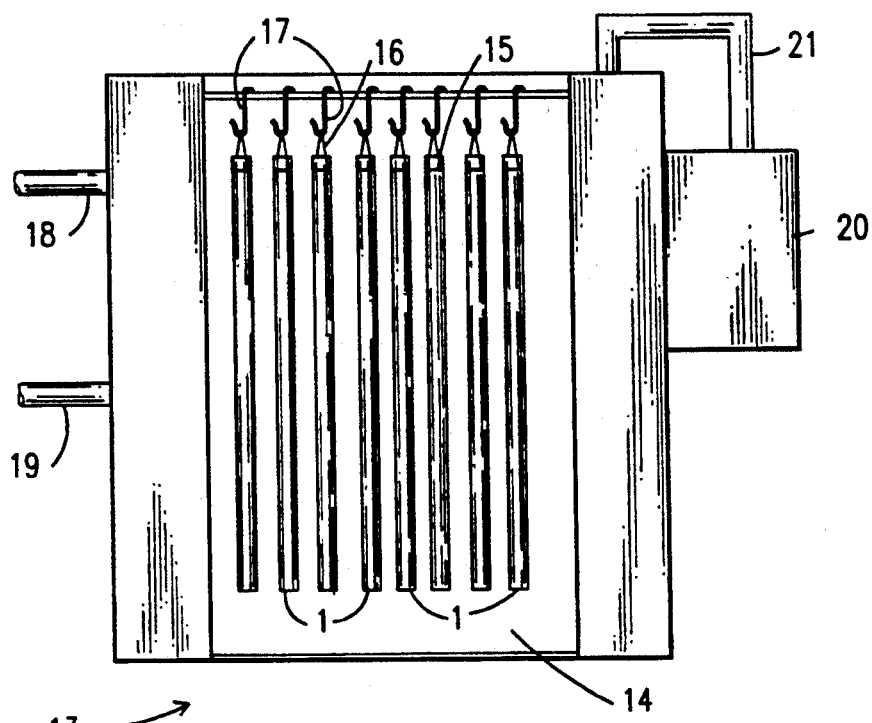
FIG. 3 is a cross-sectional elevational view of a plasma treating chamber used for preparing the surface of the tube prior to the coating operation.

FIG. 1 shows the procedural steps in applying the coating of polymeric material to the base tube of knot or woven fabric, preferably of polyester, for example, poly(ethyleneterephthalate) available commercially under the DuPont Company registered trademark "Dacron". Conventional fibers of 40–130 denier may be used but ultrafine fibers of 0.5–40 denier are preferred. Advantageously this tube initially and uncoated has a permeability of at least 200, advantageously 600–3,000, preferably 1,200–1,600 ccs. per sq. cm. per minute measured with water at approximately room temperature under a pressure of 120 mm. of Hg.

In accordance with the flow sheet of FIG. 1 one or more convenient lengths (10–90 cms.) and 1–40 mm I.D. are placed in the scrubber 7 and a number of jets 8 of deionized water are directed from the spray jets 9 on the tube or tubes as shown in FIG. 2. The jets move the tubes about while they are being scrubbed by the water streams. These tubes are removed from the scrubber by lifting lid 11 attached to the scrubber by hinge 12, and the water is drained off through exit 10 or shaken off before placing them in the dryer which is operated at about room temperature and in which is passed continuously a stream of nitrogen to remove moisture and contaminants. Then the dried tubes are placed in an oven and maintained overnight at a temperature of about 45° C. These tubes are transferred to the plasma treatment to enhance adhesion of the polymeric coating material to be added.

Where an extremely efficient cleaning procedure is used to insure an extremely clean surface on the base tube and thereby insure excellent adhesion of the coating material to the base tube, the plasma treatment may be omitted. However the plasma system is preferred to insure efficient cleaning and adhesion of the base tube surfaces. Gas plasma can clean any plastic surface and prepare it for adhesive bonding within a few minutes. It is a clean process, sues no solvents, produces no fumes and creates no disposal problems. Plasma is an excited (ionized) gas characterized by glow discharge—light emitted by the excited species, i.e., any of a multitude of free radicals and electrons, atoms and ions as they return to lower (unexcited) energy states.

Various publications describe plasma treating for this purpose, such as "Gas Plasma Technology and Surface Treatment of Polymers Prior to Adhesive Bonding" by Peter W. Rose and Edward Liston as given in a PLASTICS 85 Reprint of the Proceedings of the SPE 43rd Annual Technical Conference and Exhibition and a similar article by the same authors which appeared in PLASTICS ENGINEERING, October, 1985, pp. 41–45; "Glow Discharge Polymerization", H. Yasuda, Journal of Polymer Science, Macromolecular Reviews 16, 199 (1981); "Biomedical Applications of Plasma Polymerization And Plasma Treatment of Polymer Surfaces", H. Yasuda and M. Gazicki in "Biomaterials" 1982, Vol. 3, April; "Plasma For Modification of Polymers", H. Yasuda, Journal of Macromolecular Sci. Chem. 1976, A-10(3), 383–420.

Plasma treating equipment is available commercially. The equipment used in the examples described herein is a unit supplied by Advanced Plasma Systems, Inc. of St. Petersburg, Fla. This unit has outside dimensions of 59" length, 35" width and 72" height with an internal chamber of 38" height, 28" width and 28" depth with a power requirement of 208 volts, imput current 30 amp, 2500 watts, pump of 55 cubic feet per minute and uses argon gas. The internal chamber has a rack at the top from which the tubes to be treated can be hung vertically. A computer monitoring system is provided to monitor, record and control the various conditions in the chamber such as free radical production, volume of gas, time, etc.

FIG. 3 represents an elevational front of this type of plasma treatment unit 13 with the front door (not shown) opened or removed to show the interior of chamber 14 in which tubes 1 are hung. The tubes are open at both ends and are tied with string 15 (polyester, nylon etc.) which is formed into loop 16 to hang over hook 17. The equipment is not shown for exciting the treating gas (argon, nitrogen, carbon tetrachloride, nitrous oxide, etc.) Feed pipe 18 introduces the argon gas, etc., which is excited to generate the desired free radicals. Conduit 19 is shown for the electrical power used for this purpose. Computer 20 is used to monitor, control and record the various conditions such as free radical generator, volume of gas, time, etc. Housing 21 contains the connections between the computer 20 and the chamber 14.

After the plasma treatment in the Plasma Treatment Chamber as shown in FIG. 3, the tubes are encased in plastic bags or sheets to minimize contact with air so as to avoid recontamination before the tubes are to be introduced to the coating rollers.

Figure 4:
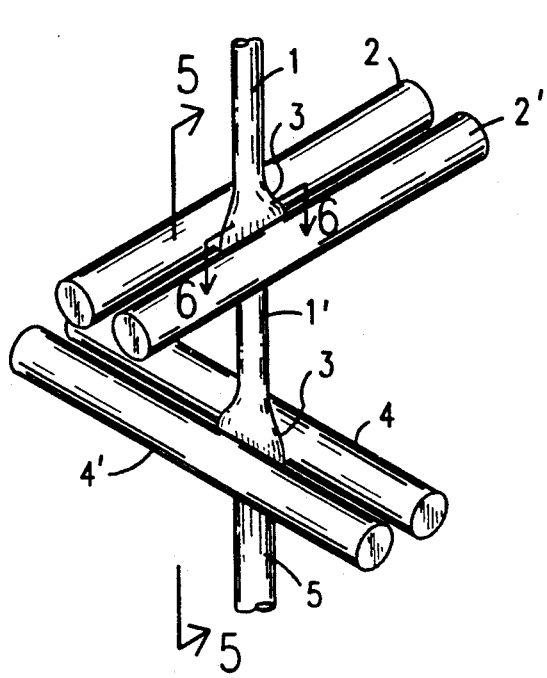
FIG. 4 is a perspective view of a coating apparatus showing two sets of two rollers each.

As shown in FIG. 4, the individual tubes are inserted between a first pair of rollers simultaneously with the introduction of viscous coating material 3 by means of a spout (not shown) around the tube as it is being pressed between the first pair of rollers 2 and 2'. The coating material 3 advantageously has a viscosity in the range of 1,000–3,500, preferably in the range of 1,500–2,500 centipoises. The coating material is pressed into the pores of the tube as the tube is pressed and substantially flattened between the first pair of rollers which are operated at a pressure of about 30–50 psi on the tube and at a rotational speed of about 6.5 seconds per revolution. The tube 1' has a preliminary coating and is fed to the second pair of rollers 4 and 4' as additional coating material 3 is introduced by means of another spout (not shown) around the tube as it is again partially flattened and pressed between the second pair of rollers. The second set of rollers is operated at a pressure of about 60–80 psi on the tube and at the same rotational speed as the first set. The fully coated tube 5 emerges from between this second pair of rollers.

Figure 5:
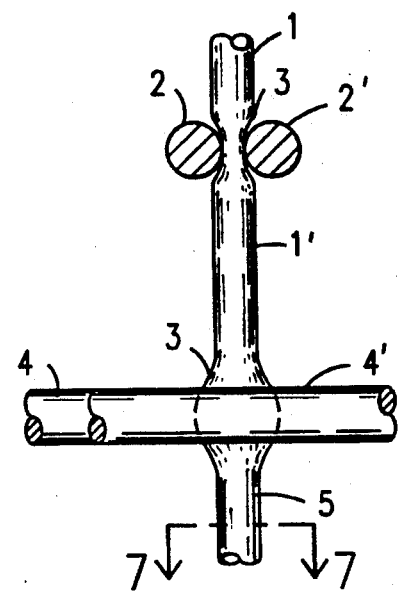
FIG. 5 is an elevational side view of the tube and a cross-sectional end view of the first set of rollers of the coating apparatus of FIG. 4.

FIG. 5 shows an end cross-sectional view of the first two pair of rollers 2 and 2' and a side view of rollers 4 and 4' with the coating material 3 being introduced around the tube 1 as it is being pressed between the two pairs of rollers.

In the arrangement shown in FIGS. 4 and 5 the two sets of rollers are arranged in opposite directions. For example, if rollers 2 and 2' are both pointing in an east-west direction, then rollers 4 and 4' are pointed in a north-south direction. Thus the second set of rollers is given a change in direction of 90° so that they are pointed in a direction of north-south with respect to the first set of rollers pointing in an east-west direction. This will effect a more even distribution of roller pressure on the coating and on the base tube. The rollers are supported at their ends and given their rotational movement at least one end thereof preferably by a cogwheel system connected to an electric motor (both of which are not shown). Obviously other rotating systems may be used to give the desired rotational speed and pressure.

The size of the rollers and the speed of rotation thereof can vary provided they accommodate the delivery, coating and pressing of the coating material into the pores of the base tube and coat the same. In the present modification, the rollers each have a diameter of about 6 cms. (about 2.36 inches) and a rotational speed of about 2.7 seconds per revolution. With a 60 cm length (and 6 mm inside diameter) a base tube can be passed through the roller system with about 3–4 rotations of each roller in about 8–15 seconds. The rollers are contained in a chamber or in a room with controlled temperature preferably about 20°–40° C. and advantageously a relative humidity of 60–80%, preferably about 70%.

Figure 6:
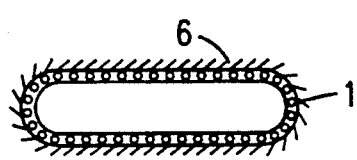
FIG. 6 is a cross-sectional end view of the tube with coating material applied as the tube passes between rollers.

FIG. 6 represents the eliptical shape given to the tube 1 and its coated surface 6 as the tue passes between the rollers.

Figure 7:
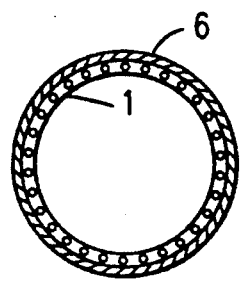
FIG. 7 is a cross-sectional view of the coated tube of this invention.

FIG. 7 shows a cross-sectional view of the tube 1 and its coated surface 6. No attempt is made to show the coating material impregnated in the interstices of the tube. Moreover these drawings are not drawn to scale and in attempting to depict the respective elements of this invention their relative sizes may be out of proportion to each other.

Figure 14:
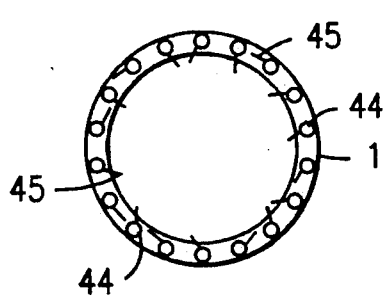
FIG. 14 is a cross-sectional view of a coated tube showing a tube having a block copolymer of polyurethane and siloxane before solvent treatment.
Figure 15:
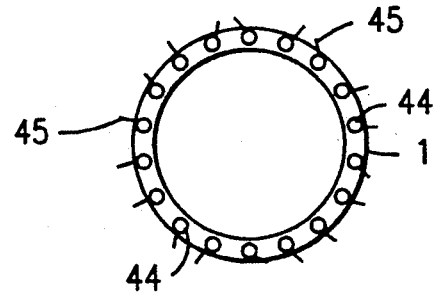
FIG. 15 is a similar view as in FIG. 14 after solvent treatment.

After the tubes are passed through the rollers with the coating applied as described above, the coated tubes are placed in the extractor for an appropriate time, generally 1–5 minutes. The extractor is a column 24 containing a solvent 25 such as an aromatic hydrocarbon, i.e., toluene, xylene, benzene, etc., or chloroform, ethylenedichloride, trichloroethane, etc. The time of extraction may be varied with the effectiveness of the solvent being used to remove the excess of coating material over that required to give the desired range of 1–25 ccs preferably of 1–5 permeability. The extraction is effected also to insure that no silicone groups are left in the interstices on the inside of the tube. Instead all silicone groups are positioned on the outer surface of the tube leaving the inside of the tube essentially of the base material of the tube such as polyester. This is illustrated by FIGS. 14 and 15. The presence of silicone groups on the blood contacting or inside of the tube has undesirable effects because of the reacting of the silicone groups.

In FIG. 8 the tubes 1 are shown arranged vertically in the extractor with the upper ends of the tubes tied with string 26 having a loop 27 looped over hooks 28 which are attached to supporting rack 29. Solvent is introduced through inlet line 30 by opening valve 31. The solvent enters the top of the extractor and falls to distributor plate 32 which has a number of openings 33. The solvent level is preferably at least high enough to completely cover the upper ends of the tubes. At the appropriate time the solvent may be removed from the extractor through the opening 34 in conical bottom 35 through exit line 36 by opening of valve 37.

The tubes are next transferred to the solvent evaporator which is a closed chamber maintained at about room temperature with inlet and outlet ports for a stream of nitrogen to be passed therethrough to sweep out evaporated solvent. After about 2 hours in this chamber the tubes are transferred to the dryer for about 60 minutes which is maintained at about 45° C.

Following the dryer, the tubes are placed in the vacuum oven which is maintained at about 60° C. and a reduced pressure of 40–50 mm of Hg for a period of about 12 hours. Curing of the coating material is effected during the periods spent in the evaporator, dryer and vacuum oven.

Figure 9:
FIG. 9 is an end view of a tube sued in the practice of this invention before any crimping treatment.

FIG. 9 shows the end view of the tube 1' prior to crimping as described herein.

Figure 10:
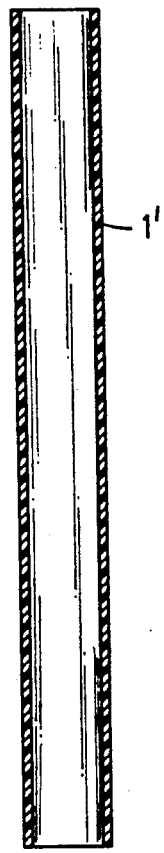
FIG. 10 is a longitudinal cross-sectional view of the tube of FIG. 10.

FIG. 10 shows a longitudinal cross-sectional view taken at line 10—10 of FIG. 9.

Figure 11:
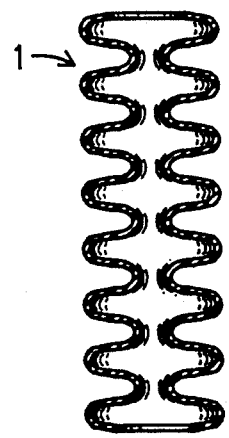
FIG. 11 is a similar cross-sectional view of the tube of FIG. 10 after crimping.

FIG. 11 shows a similar cross-sectional view of the tube of FIG. 9 after crimping with circular ridges 22.

Figure 12:
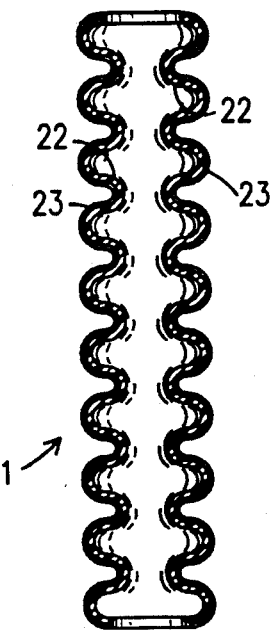
FIG. 12 is a similar cross-sectional view of the tube of FIG. 11 after the coating treatment of this invention.

FIG. 12 shows a similar cross-sectional view of the same tube after coating 23 has been applied.

Figure 13:
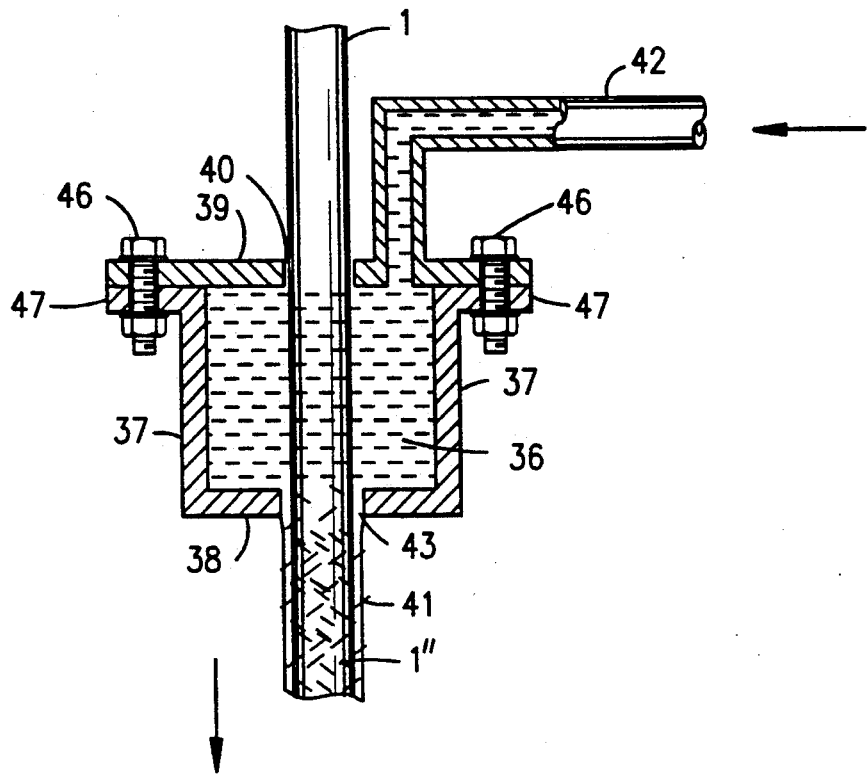
FIG. 13 is a cross-sectional view of a chamber used for applying a pressurized viscoelastic coating material to a tube.

FIG. 13 shows a convenient apparatus for applying a coating to the crimped tube 1 preferably before the coated tube is passed through the rollers in FIGS. 4 and 5. Chamber 36 is defined by walls 37, bottom 38 and top 39. Top 39 is removably fastened to flanges 47 by bolts 46. Tube 1 enters the chamber 36 through opening 40 and receives initial coating with coating material 41. Feed line 42 feeds pressurized viscoelastic coating material into chamber 36. The coated tube 1" exits from the bottom of chamber 36 through opening 43. The coated tube is subsequently passed through the rollers as shown in FIGS. 4 and 5 to receive pressure to force the coating material into the interstices of the tube 1. Chamber 36 may be insulated or provided with a heating means to maintain the coating material in soft or viscoelastic condition. This device may be of various sizes and shapes, preferably as small as possible so long as it effects the desired coating. It may be omitted when it is desired to apply the coating material manually. In such case the material may be applied just as the tube is to be passed between the rollers. The coating material may be applied just prior to entering the first set of rollers and also before entering the second set of rollers.

A separate set of rollers may be used above the coating device of FIG. 13 to slow down the entry of the tube into the coating apparatus. In such case the first set of rollers between the coating apparatus may be rotated at a faster rate of speed so that the ridges on the tube may be flattened and thereby assist in the application of coating material. Moreover if it is desired to make a continuous tube of a series of shorter tubes, a cylindrical rubber plug may be half inserted at the end of one tube and the other half of the plug inserted in the end of a second tube. In this way a number of shorter tubes may be connected for feeding into the coating apparatus. However these are preferably disconnected before the individual tubes are passed into the pressure applying first and second sets of rollers. Alternatively it may be preferable to use longer lengths of tubes and cut these into shorter lengths after the coating, extraction, etc., steps. Where the coating material is sufficiently impregnated into the interstices of the base tube by the pressurized application in the apparatus of FIG. 13, the pressurized treatment of the rollers of FIGS. 4 and 5 may be omitted.

FIG. 14 shows a cross-sectional enlarged view of tube 1 with a block copolymer of polyurethane 44 and siloxane 45 and the siloxane end of the block copolymer extending into the interior of tube 1. This is before solvent treatment.

As shown in FIG. 15 the solvent treatment causes migration of the siloxane 45 to the exterior of the tube 1. The condition shown in FIG. 15 is much preferable over that shown in FIG. 14 since the siloxane is reactive with blood and is desirably not positioned in the interior of the tube.

Figure 16:
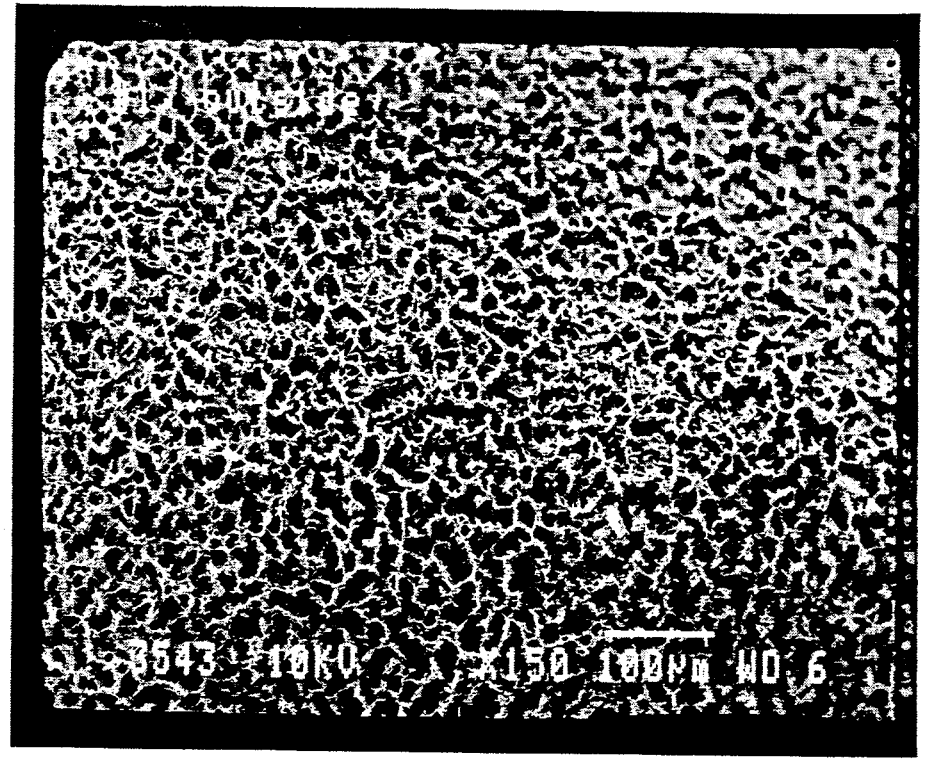
FIG. 16 is a photomicrograph of a coated tube as described for FIG. 14.
Figure 17:
FIG. 17 is a photomicrograph of the interior of the coated tube as described for FIG. 15.

FIG. 16 is a photomicrograph of the outside of a coated tube as described for FIG. 14 showing the coated outside surface at 150 magnification with an electron scanning microscope (SEM), and FIG. 17 is a similar photomicrograph of the inside of a coated tube as described for FIG. 15 showing the knitted polyester fibers.

The invention is illustrated by the following examples which are intended merely for purpose of illustration and are not to be regarded as limiting the scope of the invention or the manner in which it may be practiced. Unless specifically indicated otherwise, parts and percentages are given by weight.

EXAMPLE I

Preparation Of Hydroxybutyl-Terminated Poly(dimethylsiloxane)(HTPS)

Octamethylcyclotetrasiloxane is distilled over a molecular sieve. 4,4'-Diphenylmethane diisocyanate (MDI) is vacuum distilled at 60° C. and the distillate is precipitated in hexane maintained at 0° C. Butanediol and dimethylacetamide (DMAC) are dehydrated over calcium hydride for about 48 hours and then stripped.

1,3-Bis(4-hyroxybutyl)-tetramethyldisiloxane—(0.1 mole)—is mixed with 0.6 mole of octamethylcyclotetrasiloxane in a reaction flask equipped with a magnetic stirrer, reflux condenser, thermometer and inlet tube. Tetramethylammonium hydroxide (0.002 mole) is added and the mixture is heated to 80° C. under a nitrogen atmosphere. Stannous octoate (0.001 mole) is added and the mixture is maintained at 80° C. for 10 hours. The resulting clear fluid is then heated to 140°-145° C. for an hour to decompose the catalyst. Then the temperature is reduced to and maintained at 130° C. while a reduced pressure of less than 20 mm Hg is applied to remove any unreacted cyclic siloxane. The product is essentially of the formula:

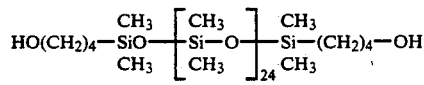

Hydroxybutyl-terminated poly(dimethylsiloxane) (HTPS)

EXAMPLE II

Block Copolymer of Polysiloxane-Urethane

The HTPS prepared above is mixed with 0.1 mole of 4,4-diphenylmethane diisocyanate (MDI) in a mixed solvent system of 3 volumes of tetrahydrofuran and 1 volume of dimethylacetamide (DMAC). Stannous octoate (0.15%) dissolved in triethylamine is then added with stirring to the HTPS-MDI reaction mixture at 60°-70° C. under a dry nitrogen atmosphere. Heating and stirring is continued at 60°-70° C. for an hour, after which 0.1 mole of chain extender, N-methyldiethanolamine (MDEA) is added and stirring continued. The polymer product is precipitated in hot water, washed with ethyl alcohol and dried in a vacuum oven at 70°-80° C. at reduced pressure of 60 mm of Hg for at least two days. A yield of approximately 95% of theoretical is obtained.

EXAMPLE III

Block Copolymer of Polysiloxane-Urethane

The procedure of Example II is repeated using in place of the MDI a polyurethane having terminal isocyanate groups, namely

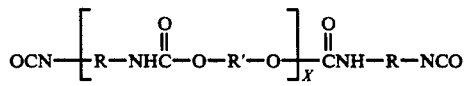

The value of X can be controlled by the relative proportions of the monomeric diisocyanate OCN—R—NCO and the glycol HO—R'—OH, where R and R' each represents divalent aromatic, aliphatic or cycloaliphic hydrocarbon groups or derivatives of such hydrocarbon groups which have substituent groups which do not interfere with any of the reactions to be performed. These R and R' groups may be referred to generically as "hydrocarbyl" groups. The number of the respective blocks can be increased by the employment of chain extenders such as N-methyldiethanolamine (MDEA), etc. For example, the use of one mole of chain extender per two moles of polymer can double the average size of the block co-polymer.

Prior to the coating procedures described below polyester knitted or woven tubes are crimped by a common heat treating procedure in which a mandrel is inserted inside the tube and then over the tube there is applied a heat shrink tube polyethylene (or other suitable material). A heat source is applied around about 2-3 inches of the tube and the heat source, such as an Infrared lamp, preferably in ring-shaped form, is moved gradually along the length of the tube. Approximately 2-3 inches of the tube is heated at each increment of movement and the lamp is between about 120° and 150° C. The lamp is advantageously moved at a rate of about 20-30 seconds at a particular point. The polyethylene shrinks upon heating and forces the textile into the grooves. If the polyethylene is not completely shrunk in any area, the heating unit is passed again in that area. The heat shrinkage provides circular ridges around the tube which are perpendicular to the longitudinal axis of the tube. For a tube having an original length of about 90 cm. the crimped tube may shrink, for example, to about 45 cm, and is compliant and very elastic. The shrinking of polyethylene is performed in an enclosed chamber to avoid conventional changes in temperature. The tube and mandrel are allowed to set for 5-15 minutes for cooling down from about 120° C. to room temperature. Then the polyethylene crinkled tube is pulled off the mandrel. After the coating treatment as applied hereafter the length may be about 60 cm with less lengthwise elasticity and is very resistant to kinking. The outside coating provides smooth blood flow surface. The coated tube has good elasticity in both longitudinal and in transverse direction (hoop stress). Preferably there are generally about 8-12 crimps per inch of length of tube. In addition to other advantages these coated tubes allow easy passage of needle and suture and thereby facilitate their implacement as artificial blood vessels. In addition to the concentric type of crimped tube, those having a continuous spiral ridge may also be used.

EXAMPLE IV

Five knit polyester tubes crimped as described above and having a length of approximately 60-90 cm, an inside diameter of 4-6 mm, and a permeability of 1,000-1,200, made originally from polyester fiber of approximately 2-10 denier are scrubbed, dried, heated in the oven at about 45° C. overnight and then plasma treated as described above. Then the tubes are run individually through the coating rollers as shown in FIGS. 4 and 5 using the coating composition prepared in Example II which has a viscosity of about 2000 centipoises. The amount of coating material is measured in a measuring jar and the amount added through a spout onto the tube as it passes through each pair of rollers is about 500 milliliters. The coated tubes are then treated with toluene in the extractor for 5-6 minutes to remove excess coating material. Then the tubes are placed in the solvent evaporator at about 40° C. for a period of about 2 hours where solvent vapors are removed in a stream of nitrogen. Next the tubes are placed in the dryer maintained at about 45° C. under a stream of nitrogen for about 60 minutes. Finally the tubes are placed in the vacuum oven which is maintained at about 60° C. and a reduced pressure of 40-50 mm of Hg for about 12 hours. By the end of the vacuum treatment the coating material has satisfactorily cured. Each tube is then sealed at one end and the other end fastened to a device for feeding water and measuring the water pressure. The amount of water permeating through the wall of the tue and the number of minutes tested are determined. From the outer area of the tube there is calculated the amount of water permeating per sq. cm of surface per minute. For the five tubes tested, the permeability for each tube is determined to be in the range of 1-5 cubic centimeters of water per sq. cm of surface per minute and are suitable for use as artificial blood vessels. The permeability of the uncoated tube was originally determined to be in the range of 1,200-1,600 cubic centimeters or milliliters of water per sq. cm of surface per minute.

Similar results are obtained when the above procedure is repeated using an equimolar amount of 1,4-butylene glycol as the chain extender in place of the N-methyldiethanolamine (MDEA).

In the event the permeability is higher than desired after the course of the treatments described above, the coating and subsequent steps may be repeated using a smaller amount of the coating material. This may be repeated as often as required to obtain the desired permeability.

In the event the coated tubes are impermeable or below the desired amount, the solvent extracting and subsequent steps maya be repeated until the desired permeability is reached.

As previously stated, if polysiloxane is used by itself, that is if there is only one layer comprising only polysiloxane, the amount of material required to reduce the permeability to the desired range is such that the pores are penetrated and the polysiloxane is forced into the interior surface of the base tube with various undesirable results. Therefore in order to produce the desired permeability when the first layer consists of polysiloxane, at least a second layer should be applied of either polyurethane or a block copolymer.

When reference is made to a "layer", this may comprise the addition of one or more coatings of the same material. In some cases it may be necessary to apply two or more coatings to obtain the desired properties or thickness of the layer.

For example a single polyurethane layer may require the application of 4-5 coatings of polyurethane to obtain the desired reduction in permeability. In other cases one coating with polysiloxane may be used to give a first layer, and then a second layer of polyurethane applied by the application of 2-3 coatings with polyurethane to give the desired permeability without an undesirable amount of coating material penetrating through the pores into the interior of the tube. In other cases a layer of block copolymer generally by one coating may give sufficient reduction in permeability to reach the desired range.

When it has been found that a number of coatings with the same or different materials is desired to give the appropriate permeability, the coating step may be repeated the appropriate number of times before the subsequent treating steps are performed. However, where it has been found after the subsequent treating steps that the permeability has not been sufficiently reduced, it is suitable to repeat the coating steps and then again the subsequent treating steps.

The following table outlines the combination of layers that may be used satisfactorily in the practice of the invention (each layer may be applied by one or more coatings):

| | Layers | |
|---|---|---|
| 1st | 2nd | 3rd |
| Polysiloxane | Block copolymer | — |
| " | " | Polyurethane |
| " | " | Polysiloxane |
| " | Polyurethane | — |
| " | " | Block copolymer |
| " | " | Polysiloxane |
| Polyurethane | — | — |
| " | Polysiloxane | |
| " | " | Block copolymer |
| " | " | Polyurethane |
| " | Block copolymer | — |
| " | " | Polysiloxane |
| " | " | Polyurethane |
| Block copolymer | — | — |
| " | Polysiloxane | |
| " | Polyurethane | — |
| " | Polysiloxane | Polyurethane |
| " | " | Block copolymer |
| " | Polyurethane | Polysiloxane |
| " | " | Block copolymer |

The molecular weights of the polymeric materials used for the coating purposes of this invention are advantageously in the range of 1500-300,000 preferably 2,000 to 250,000 with desired viscosities in the range of 1,000-3,000, preferably 1,500-2,500 centipoises. In the block copolymer, the preferred ranges of components is 10-50 percent by weight of polysiloxane and 50-90 percent by weight of polyurethane. Increase in the percentage of polysiloxane increases the number of coatings required and also increases the stiffness of the resultant graft. As this stiffness increases the suturability passage of needle and suture is impaired.

Improved elasticity is attributed to the method of manufacture by the practice of this invention and also in decreasing polysiloxane content. When the graft containing 100 percent polysiloxane is introduced into the body, it is believed that calcification or thickening of the walls of the graft may be due to the deposition of calcium deposits.

The products of this invention are elastic, mechanically strong and tear resistant. They generally do not require reinforcing filler, nor the host of stabilizers and antioxidonts generally otherwise necessary to make them body compatible. They are good to excellent with respect to blood contact. The solvent extraction step in the procedure described above gives an excellent smoothness to the coating.

The biologic surface which ultimately develops after active transport of ions is called a neointima, is formed from the seeding out of blood elements (platelets, cells and fibrin), from perigraft tissue ingrowth and from pannus ingrowth longitudinally from the host vessel.

The surface of the artificial blood vesel or graft may be passivated to flowing blood, but unless covered by endothelium is unstable and thrombogenic. If flow is comprised in nonendothelial lined conduits, even momentarily, catastrophic events may occur leading to complete occlusion of the graft.

One feature which distinguishes the graft or artificial blood vessel of the present invention is the presence of a cellular endothelial lining. This lining, in addition to being nonthrombogenic, is capable of repair and renewal.

EXAMPLE V

The procedure of Example IV is repeated using as the coating material the block copolymer of Example III in which R is phenylene, R' is butylene, X has a value of 500 and the polymeric material has a viscosity of 3,500 centipoises. The permeability of the coated tubes after full treatment are each in the range of 1-5 cubic centimeters per sq. cm. of surface per minute and are suitable for use as artificial blood vessels.

EXAMPLE VI

The procedure of Example IV is repeated using as the coating material a poly(dimethyl siloxane) material having a viscosity of 2,500 centipoises. Over the layer of polysiloxane there is applied a coating of the block copolymer used in Example II. The coated tubes have a permeability in the range of 1-5 cubic centimeters per sq. cm. of surface per minute and are suitable for use as artificial blood vessels.

EXAMPLE VII

The procedure of Example IV is repeated using four coatings of a polyurethane made from MDI and 1,4-butylene glycol having a viscosity in the range of 1800 centipoises. The coated tubes have a permeability in the range of 1-5 cubic centimeters per sq. cm. of surface per minute and suitable for use as artificial blood vessels.

EXAMPLE VIII

The procedure of Example VII is repeated using two coatings of the polyurethane and then a layer of the block copolymer of Example II is applied. The permeability of the coated tubes is in the range of 1-5 cubic centimeters and these tubes are suitable for use as artificial blood vessels.

EXAMPLE IX

The procedure of Example VI is repeated except that over the coating of the block copolymer there is applied a coating of the polyurethane used in Example VII. Again the coated tubes have a permeability in the range of 1-5 cubic centimeters per sq. cm. of surface per minute and are suitable for use as artificial blood vessels.

EXAMPLE X

The procedure of Example IV is repeated except that hydroxybutyl-terminated poly(dimethylsiloxane) used in Example I for the preparation of the block copolymer of Example II is prepared by substituting an equivalent amount of decamethylcyclopentasiloxane in place of the octamethylcyclotetrasiloxane. The tubes coated with this block copolymer have a permeability in the range of 1-5 cubic centimeters per sq. cm. of surface per minute and are suitable for use as artificial blood vessels.

EXAMPLE XI

The procedure of Example X is repeated 6 times except that equivalent amounts of the following cyclic compounds respectively are used independently in substitution for the octamethylcyclotetrasiloxane:
 (a) Hexamethylcyclotrisiloxane;
 (b) Octaphenylcylcotetrasiloxane;
 (c) Trimethyltriphenylcyclotrisiloxane;
 (d) Tetravinyltetramethylcyclotetrasiloxane;
 (e) Trimethyltri(trifluoropropyl)cyclotrisiloxane;
 (f) Tetramethyltetrahydro cyclotetrasiloxane
In each case the coated tubes have a permeability in the range of 1-5 and is suitable for use as artificial blood vessels.

EXAMPLE XII

The procedure of Example IV is repeated four times using in each case a different fiber in the base tube with corresponding denier and other conditions, these fibers being:
 (a) Polyurethane
 (b) Nylon
 (c) Rayon
 (d) Polyproylene
In each case the coated tubes have a permeability in the range of 1-5 and is suitable for use as artificial blood vessels.

While cylipolysiloxanes are a convenient starting material for preparing hydroxyhydrocarbylpolysiloxane compounds for incorporation into block copolymers, other method for preparing such block copolymers are also suitable for use in the practice of this invention.

Moreover the polyisocyanates, preferably diisocyanates, useful in the polyurethanes used as such or in the block copolymers may be prepared from a a variety of such compounds such as 1,5-naphthalene diisocyanate;

3,3'-bitoluene diisocyanate; methylene bis(p-cyclohexylisocyanate) 2,7-octane diisocyanate; 4,4'-diphenyl diisocyanate; etc.

In addition to the chain extenders used above, others may be used such as ethylenediamine; 4,4'methylene-bis(2-chloroaniline); ethylene glycol, propylene glycol; hexanediol, 1,3-propylenediamine; etc.

Furthermore in addition to the siloxanes used above others are also suitable in which various other groups are attached to the Si atom such as methyl, phenyl, trifluoropropyl, hydride, hydroxy, aminopropyl, aminobutyl, tolyl, cyclohexyl, butyl, hexyl, propyl, etc.

EXAMPLE XIII

Apparatus as shown in FIG. 13 is used to apply polymeric coating material to a polyester crimped tube as described herein. A means of resistance, such as a pair of rollers, is applied to the tube before its entrance into the chamber so as to provide slight resistance to the passage of the tube therethrough thereby requiring a pull on the lower part of the tube which pull flattens the ridges on the exterior surface and thereby improving exposure of the surface for the application of the coating. For introduction of the tube into the chamber a steel rod may be inserted snugly into the lower open end of the tube and the steel rod forced downward into the molten mass in the chamber until the lower end of the tube passes through the exit opening at the bottom of the chamber after which the steel rod may be removed from the tube. Openings 40 and 43 may be equipped with adjustable inlet and outlet ports (not shown) to accommodate tubes of different diameters. Exit opening 43 is slightly larger to allow for the thickness of the coating on the tube. Chamber 36 has a diameter of 8 inches and a height of 12 inches. Feed line 42 has an inside diameter of 2 inches and under a pressure of 30-50 psi feeds viscoelastic coating material at a temperature high enough to maintain the coating material at a viscosity in the range of 1000-3500 centipoises. Top 39 is removably fastened by bolts 46 to flanges 47 so that the top may be removed for cleaning of the chamber whenever desired. Chamber 37 is insulated to prevent loss of heat from the viscoelastic material. The chamber may be provided with a heating means (not shown) in case it is necessary or desired to compensate for heat loss and to keep the coating material in the appropriate viscosity range. This apparatus is used in place of the rollers in applying the coating material as described above in Examples IV-XII with satisfactory results. This apparatus is also used prior to and in combination with the rollers of FIGS. 4 and 5 with the coating materials of Examples IV-X, again with satisfactory results.

While no more than three layers have been described in the above examples there is no reason why more such layers may not be used. Three layers or less are more practical but with thin layers and appropriate permeability additional layers may be used.

Moreover where a plurality of coatings are applied, these are preferably applied prior to the solvent extraction. However where it is considered desirable to add coatings after the subsequent treatment steps, additional coatings may still be applied followed by a repetition of the subsequent treatment.

Furthermore while the use of an extractant is preferred because it enhances the uniformity and smoothness of the exterior surface of the resultant tube, and effects leaching out of impurities, it is possible to omit the solvent treatment and reach the desired range of permeability by applying a greater number of thinner coats. Where the foregoing advantages are not desired or required, the solvent treatment may be omitted.

While certain features of this invention have been described in detail with respect to various embodiments thereof, it will of course be apparent that other modifications can be made within the spirit and scope of this invention and it is not intended to limit the invention to the exact details shown above except insofar as they are defined in the following claims.

The invention claimed is:

1. A process for preparing an artificial blood vessel, comprising: providing a base tube having a crimped external surface, said base tube being made of fibers having interstices therebetween, coating the external surface of the base tube with at least one layer of a polymeric material selected from the group consisting of polyurethanes, polysiloxanes, block copolymers of polysiloxane and polyurethane, and combinations thereof, while at the same time maintaining a sufficient pressure to cause said polymeric material to enter the interstices between the fibers of the base tube until a coated tube has a reduced permeability of about 1-25 cubic centimeters of water per square centimeter of exterior surface of said tube per minute measured under 120 millimeters of Hg, provided that where said at least one layer of the polymeric material is a polysiloxane a layer of one other of the polymeric materials of said group other than a polysiloxane is applied to the layer of polysiloxane while maintaining said pressure.

2. The process of claim 1 wherein the polymeric material is viscoelastic.

3. The process of claim 1 wherein said tube is fed between at least two pairs of rotatable rollers, each pair of said rollers being positioned parallel to and in side-by-side relation to each other, each of said at least two pairs of rollers being arranged in spaced relation to one another and having their longitudinal axes positioned at an angle to each other, said polymeric material being applied to said tube as it passes between said first pair of rollers and said second pair of rollers, said second pair of rollers being rotated at a rate of speed different than the rate of rotation of the first pair of rollers, each pair of said rollers acting to apply pressure to said tube as it passes therebetween whereby said coating material is caused to enter into the interstices of the fibers of said tube.

4. The process of claim 3 in which prior to being passed through said rollers said tube is passed through a chamber in which a first coating of said polymeric material is viscoelastic and is applied under pressure to the external surface of said tube.

5. The process of claim 1 in which said fibers are polyester.

6. The process of claim 1 in which said fibers are poly(ethyleneterephthalate).

7. The process of claim 6 in which the permeability of said tube is reduced to 1-5 cubic centimeters of water per square centimeter of exterior surface of said tube per minute measured under 120 millimeters of Hg.

8. The process of claim 7 in which the permeability of said tube prior to the application of said coating is greater than 1,000 cubic centimeters.

9. The process of claim 7 in which the permeability of said tube prior to the application of said coating is in the range of 1,000-3,500.

10. The process of claim 7 in which the permeability of said tube prior to the application of said coating is in the range of 1,000–1,600.

11. The process of claim 1 in which said base tube is prior to the application of said polymeric material coating is cleaned by a plasma treatment.

12. The process of claim 1 in which said fibers are polyester.

13. The process of claim 1 in which said fibers are poly(ethyleneterephthalate).

14. The process of claim 1 in which said coating contains a layer of a block copolymer comprising at least one block of a polysiloxane and at least one block of a polyurethane.

15. The process of claim 1 in which said coating contains a layer selected from the group consisting of polysiloxane and polyurethanes.

16. The process of claim 14 in which said block copolymer is the reaction product of an hydroxybutyl-terminated polysiloxane with an aromatic diisocyanate.

17. The process of claim 3 in which the longitudinal axes of each of said pairs of rollers are positioned at approximately 90° with relation to one another.

18. The process of claim 3 in which there are three pairs of rollers arranged in spaced, angled relation to one another.

19. The process of claim 3 in which the rate of rotation of the rollers in said second pair is faster than the rate of rotation of the rollers in said first pair whereby the crimped external surface of said tube are substantially flattened in the length of tube between said first pair and said second pair.

20. The process of claim 17 in which the rate of rotation of the rollers in said second pair is faster than the rate of rotation of the rollers in said first pair whereby the crimped external surface of said tube are substantially flattened in the length of tube between said first pair and said second pair.

21. The process of claim 18 in which the rate of rotation of each pair of rollers is different than the rate of rotation of each of the other pairs of said rollers whereby the crimped external surface of the tube is flattened between each of said pairs of rollers.

* * * * *